United States Patent [19]

Bravo et al.

[11] Patent Number: 6,096,306

[45] Date of Patent: Aug. 1, 2000

[54] **STRAINS OF *BACILLUS THURINGIENSIS* AND PESTICIDE COMPOSITION CONTAINING THEM**

[75] Inventors: Alejandra Bravo, Morelos, Mexico; Didier Lereclus; Hervé Agaisse, both of Paris, France; Sylvie Salamitou, Maule, France; Vincent Sanchis, Paris, France

[73] Assignees: Institut Pasteur; Institut National de la Recherche Agronomique, both of Paris, France

[21] Appl. No.: 09/051,914

[22] PCT Filed: Oct. 28, 1996

[86] PCT No.: PCT/FR96/01684

§ 371 Date: Jul. 2, 1998

§ 102(e) Date: Jul. 2, 1998

[87] PCT Pub. No.: WO97/15677

PCT Pub. Date: May 1, 1997

[30] Foreign Application Priority Data

Oct. 27, 1995 [FR] France ................... 95 12741

[51] Int. Cl.⁷ .......................... A01N 63/00; A61K 48/00; C12N 1/20

[52] U.S. Cl. ................... 424/93.461; 424/93.2; 435/252.5

[58] Field of Search ................. 424/93.1, 93.2, 424/93.461; 435/252.5

[56] References Cited

U.S. PATENT DOCUMENTS 5,262,159  11/1993  Payne et al. ................... 424/93

FOREIGN PATENT DOCUMENTS

| | | |
|---|---|---|
| 0 178 151 | 4/1986 | European Pat. Off. . |
| 0 192 319 | 8/1986 | European Pat. Off. . |
| 0 224 331 | 6/1987 | European Pat. Off. . |
| 0 228 838 | 7/1987 | European Pat. Off. . |
| 0 295 156 | 12/1988 | European Pat. Off. . |
| 0 349 353 | 1/1990 | European Pat. Off. . |
| 4-335894 | 11/1992 | Japan . |
| WO 82/03872 | 11/1982 | WIPO . |
| WO 93/02199 | 2/1993 | WIPO . |
| WO 94/25612 | 11/1994 | WIPO . |

OTHER PUBLICATIONS

Adams et al. Molecular Cloning and Characterization of Two Genes Encoding Sigma Factors that Direct Transcription from a *Bacillus thuringiensis* Crystal Protein Gene Promoter. J. Bacteriology 173:3846–3854, Jun. 1991.

Lereclus et al. Overproduction of Encapsulated Insecticidal Crystal Proteins in a *Bacillus thuringiensis* spo0A Mutant. Bio/Technology 13:67–71, Jan. 1995.

Baum et al. Regulation of Insecticidal Crystal Protein Production in *Bacillus thuringiensis*. Molecular Microbiology 18(1):1–12, 1995.

Lee F. Adams et al, "Molecular Cloning and Characterization of Two Genes Encoding Sigma Factors That Direct Transcription From a *Bacillus thuringiensis* Crystal Protein Gene Promoter", Journal of Bacteriology, vol. 173, No. 12, pp. 3846–3854,, Jun. 1991.

Alejandra Bravo et al, "Analysis of cryLAa Expression of sigE and sigK Mutants of *Bacillus thuringiensis*," Mol Gen Genet 1996 250:734–741.

(List continued on next page.)

*Primary Examiner*—Karen Cochrane Carlson
*Assistant Examiner*—Devesh Srivastava
*Attorney, Agent, or Firm*—Oblon, Spivak, McClelland, Maier & Neustadt, P.C.

[57] ABSTRACT

The present invention relates particularly to a strain of *Bacillus thuringiensis* characterized in that it expresses the gene sigma E (σE) and does not sporulate at all or little sporulates or does not produce any viable spores. The invention also relates to a pesticide composition containing said strain of *Bacillus thuringiensis*.

19 Claims, 6 Drawing Sheets

OTHER PUBLICATIONS

H. Agaisse, et al., Journal of Bacteriology, vol. 176, No. 15, pp.4734–4741, "Expression in *Bacillus subtilis* of the *Bacillus thuringiensis* crylllA Toxin Gene is not Dependent on a Sporulation–Specific Sigma Factor and is Increased in a spoOA Mutant", Aug. 1994.

H. Agaisse, et al., Molecular Microbiology, vol. 13, No. 1, pp. 97–107, "Structural and Functional Analysis of the Promoter Region Involved in Full Expression of the crylllA Toxin Gene of *Bacillus thuringiensis*", 1994.

W. Donovan, et al., J. Mol. Biol., vol. 196, pp. 1–10, "Genes Encoding spore Coat Polypeptides from *Bacillus subtilis*", 1987.

H.T. Dulmage, Journal of Invertebrate Pathology, vol. 15, pp. 232–239, "Insecticidal Activity of HD–1, a New Isolate of *Bacillus thuringiensis* Var. Alesti", 1970.

M.–M. Lecadet, et al., Journal of General Microbiology, vol. 121, pp. 203–212, "Generalized Transduction in *Bacillus thuringiensis* Var. Berliner 1715 Using Bacteriophage CP–54Ber",1980.

D. Lereclus, et al., Mol. Gen. Genet., vol. 204, pp. 52–57, "Identification of Tn4430, a Transposon of *Bacillus thuringiensis* Functional in *Escherichia coli*", 1986.

D. Lereclus, et al., Molecular Microbiology, vol. 204, pp. 35–46, "spbA Locus Ensures the Segregational Stability of pTH1030, a Novel Type of Gram–Positive Replicon", 1992.

D. Lereclus, et al., FEMS Microbiology Letters, vol. 60, pp. 211–217, "Transformation and Expression of a Cloned δ–Endotoxin Gene in *Bacillus thuringiensis*", 1989.

I. Lopez–Diaz, et al., Journal of General Microbiology, Vol. 132, pp. 341–354, "spollD Operon of *Bacillus subtilis*: Cloning and Sequence", 1986.

T. Msadek, et al., Journal of Bacteriology, vol. 172, No. 2, pp. 824–834, "Signal Transduction Pathway Controlling Synthesis of a Class of Degradative Enzymes in *Bacillus subtilis*: Expression of the Regulatory Genes and Analysis of Mutations in degS and degU", Feb., 1990.

S. Rong, et al., Journal of Bacteriology, vol. 165, No. 3, pp. 771–779, "Transcriptional Control of the *Bacillus subtilis* spollD Gene", Mar. 1986.

V. Sanchis, et al., Molecular Microbiology, vol. 2, No. 3, 12 pp., "Multiplicity of δEndotoxin Genes with Different Insecticidal Specificities in *Bacillus thuringiensis*Aizawai 7.29", 1988.

V. Sanchis, et al., Molecular Microbiology, vol. 3, No. 2, pp. 229–238, "Nucleotide Sequence and Analysis of the N–Terminal Coding Region of the Spodoptera–Active δ–Endotoxin Gene of *Bacillus thuringiensis*Aizawai 7.29", 1989.

K.Sandman, et al., J. Mol. Biol., vol. 200, pp. 461–473, "Identification of the Promoter for a Spore Coat Protein Gene in *Bacillus subtilis* and Studies on the Regulation of its induction at a Late Stage of Sporulation", 1988.

P. Trieu–Cuot, et al., Gene, vol. 23, pp. 331–341, "Nucleotide Sequence of the *Streptococcus Faecalis* Plasmid Gene Encoding the 3'5"–Aminoglycoside Phosphotransferase Type III", 1983.

R. Villafane, et al., Journal of Bacteriology, vol. 169, No. 10, pp. 4822–4829, "Replication Control Genes of Plasmid pE194", Oct., 1987.

H.C. Wong, et al., The Journal of Biological Chemistry, vol. 258, No. 3, pp. 1960–1967, "Transcription and Translational Start Sites for the *Bacillus thuringiensis* Crystal protein Gene", Feb. 10, 1983.

M. Young, et al., Early Events During Bacterial Endospore Formation, pp. 103–162, 1979.

H. Yoshisue, et al., Gene, Vol. 137, pp. 247–251, "Identification of a Promoter for the Crystal Protein–Encoding Gene crylVB From *Bacillus thuringiensis* Subsp. Israelensis", 1993.

H. Yoshisue, et al., Journal of Bacteriology, vol. 175, No. 9, pp. 2750–2753, "Transcriptional Regulation of *Bacillus thuringiensis* Subsp. Israelensis Mosquito Larvicidal crystal Protein Gene crylVA", May, 1993.

FIG. 1

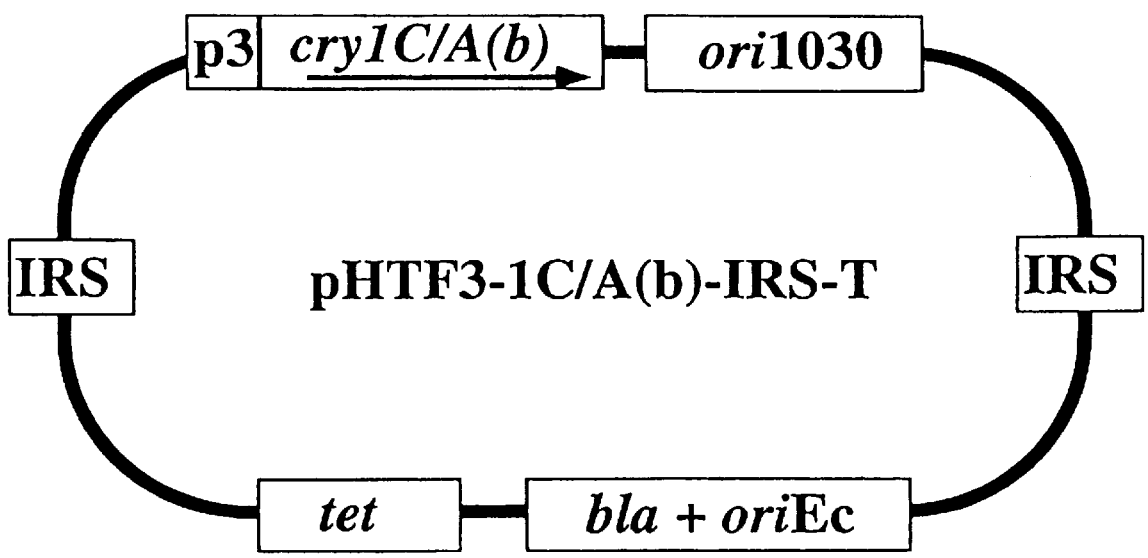
FIG_5

Specific recombination site catalyzed *in vivo* by TnpI in the absence of selection pressure for tetracycline

SEQUENCE LISTING

```
<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
cccaagcttg caggtaaatg gttctaac                                  28

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
cgcggatcca tctcttttat taagatacc                                 29

<210> SEQ ID NO 3
<211> LENGTH: 31
<212> TYPE: DNA
```

<213> ORGANISM: Artificial Sequence
<220> FEATURE:
<223> OTHER INFORMATION: Description of Artificial Sequence:Synthetic
      DNA

<400> SEQUENCE: 3
cgggatcccg ttgaaagcgt agaggtcaga a                              31

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
gctctagagc caacgcgatg catatgttgc ta                             32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ggaattccat tgtctgacgt gttaggtaca                                30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
cgggatcccg atacgcaata tctcgcaatg a                              31

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
cgggatcccg tccagttata atttgagctc caa                            33

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
gctctagagc cccgattgta ccaattgaaa t                              31

<210> SEQ ID NO 9
<211> LENGTH: 30
<212> TYPE: DNA
<213> ORGANISM: Artificial Sequence -continued

```
<220> FEATURE:
<223> OTHER INFORMATION: Description of Artificial Sequence:Synthetic
      DNA

<400> SEQUENCE: 9
ggaattccat taaagcgatc gagagctatt                                          30

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
cgggatcccg gcaccttcta atattacaga tagaa                                    35

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
ttttctaaaa agcgtattga a                                                   21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ggagaaacca tagttatgaa                                                     20
```

STRAINS OF *BACILLUS THURINGIENSIS* AND PESTICIDE COMPOSITION CONTAINING THEM

The present invention relates to novel strains of *Bacillus thuringiensis*, cesticidal compositions employing them as well as the use of these strains for the expression of proteins of interest.

*Bacillus thuringiensis* (Bt) is a Gram-positive bacterium which produces proteins having insecticidal properties, especially against larvae of a large number of insects. These bacteria, possibly after inactivation, are used in pesticidal compositions intended to combat insects harmful to crops or vectors of disease, especially mosquitoes.

At present, Bt serotype 3a 3b especially is used against crop pests, and the serotype H14 is used to destroy mosquito larvae.

The proteins with pesticidal activity produced by *Bacillus thuringiensis* are called δ-endotoxins and are produced abundantly during sporulation. They accumulate in the form of parasporal crystalline inclusions, and can represent up to 25% of the dry weight of the sporulated cells.

Numerous genes of δ-endotoxins have been cloned, sequenced and classified in five groups and in various subgroups on the basis of sequence homologies and of the toxicity spectrum. The corresponding genes are called cry genes.

Formulations based on *Bacillus thuringiensis* have been used as biopesticides for close to 30 years under different trade names. The use of *Bacillus thuringiensis* as a biological control agent has numerous advantages with respect to chemical pesticides; in fact, it has a narrow and very specific host spectrum and it is without effect on the insects which are not targets and it is without unfavorable effect on vertebrates or on the environment.

However, the slight persistence of the δ-endotoxins in the environment and the presence of spores in the formulations represent two disadvantages for the marketing of products based on *Bacillus thuringiensis*. In order to resolve these two problems, it has been proposed in the patent application EP-192 319 to encapsulate the toxins in cell membranes, in particular using Pseudomonas fluorescens-type cells expressing the Cry1Ac toxin, or alternatively in the patent application PCT W094/25612, by expressing the Cry1IIA toxin in an affected nonsporulating mutant in the spo0A gene. This latter strategy is possible because the mode of expression of the cryIIIA gene is different from the mode of expression of other cry genes, in fact this cryIIIA gene is expressed from a promoter whose activation is independent of all the genes involved in the initiation of sporulation or of the factors involved in sporulation.

In *Bacillus thuringiensis*, the sporulation is dependent on the expression of two sigma factors respectively called sigma [σ]35 and sigma [σ]28; account having been taken of their great homology with the sigma (σ)E and sigma (σ)K factors in *Bacillus subtilis*, it is this latter terminology which will be used below, in the same way as the corresponding genes will be called sigE and sigK.

The present invention relates to a strain of *Bacillus thuringiensis* which expresses σE but does not sporulate or sporulates little or does not produce viable spores.

The present invention is based on the demonstration of the fact that a mutant of *Bacillus thuringiensis* which expresses sigE and which does not express sigK produces a quantity of toxins virtually identical to the corresponding wild strain, but, on the other hand, does not sporulate or does not produce viable spores.

This is particularly the case when the strain is a sigK⁻ strain.

The construction of such strains has two advantages: 1) avoiding the dissemination of spores into the environment during treatment with biopesticides; 2) increasing the persistence of the toxins in the environment because of their encapsulation.

Tests have shown that a Bt strain not expressing the sigma K gene sigK⁻) was capable of accumulating a quantity of toxins equivalent to the source strain, while not producing spores. It was capable of producing the virtual totality of the toxins encoded by the cry genes or the related genes whose expression is dependent on the production of the σE protein.

In order to obtain sigK⁻ mutants of Bt, it is particularly advantageous to use an interruption technique, by insertion or deletion or change of phase of the sigK gene by introducing any DNA sequence, it being possible, in addition, to choose this DNA sequence so as to confer a selection character on the mutant; it could be, for example, resistance to an antibiotic, especially to kanamycin, which would allow strains which have been subjected to interruption to be selected.

The sigK⁻ mutants can likewise be obtained by the deletion of all or part of the nucleotide sequence corresponding to that of the sigK gene with or without regulatory regions.

The techniques of interruption of genes are known, they consist essentially in introducing, at the level of a DNA sequence carrying the sigK gene, any DNA sequence, the whole being introduced into the strain produces a homologous recombination, the sigK gene being replaced by the interrupted sigK gene. The selection character allows mutants of interest to be selected at this time.

Of course, it is particularly advantageous to choose, as strains intended to be transformed, strains of *Bacillus thuringiensis* having a very varied or very significant toxin production. In fact, as has been indicated above, the fact of interrupting the sigK gene only blocks sporulation but does not block the production of the toxins.

Bt is understood as meaning any strain of *Bacillus thuringiensis*.

Thus, among the strains intended to be subjected to interruption, the industrial strains could be used.

For example, Bt subsp. *kurstaki* HD-1 described by Dulmage H. T. (1970), or *Bt israelensis*, or a wild strain such as *Bt aizawai* 7–29 (this strain is accessible to IEBC under the No. T07029).

The present invention relates more particularly to the strain *Bacillus thuringiensis* 407 SigK⁻ (pHT410) as well as the recombinant strain *Bacillus thuringiensis* Kto SigK⁻ (pHTF3-1C/A (b)-IRS-T-Δ) deposited in the National Collection of Microorganism Cultures of the Institut Pasteur 28 Rue du Doctor Roux, on Oct. 26, 1995 under the No. I-1634 and on Oct. 22, 1996 under the No. I-1776 respectively.

It is likewise possible, in order to increase the production of toxins, to introduce into the sigK⁻ strains according to the invention self-replicating plasmid systems ensuring the expression of the said toxins according to constructs which are likewise known to the expert.

The proteins expressed by the strain could depend on the type of pesticidal activity sought, thus Cry1 is toxic for Lepidoptera, Cry1I against Lepidoptera and Diptera and Cry1V against Diptera.

Generally speaking, it is possible to produce sigK⁻ of the wild strains which naturally express a certain number of toxins such as cryIC, cryIA, cryIVA,B,D. It is likewise possible to use mutant strains such as described according to the invention which are sigK⁻ and which express, after chromosomal or plasmid integration, genes coding for homologous or heterologous proteins with respect to the Bt genome.

An illustration of the technique utilizable is described in Biotechnology, 1992, vol. 10, p. 418 (Lereclus et al.).

It is possible to introduce a gene, for example the cryIC gene, into the Bt sigK⁻ strain by homologous recombination. The recombinant acquires the cryIC gene and does not retain any foreign DNA.

Several toxin genes can thus be added, either in the bacterial chromosome by homologous recombination, or integrated on resident plasmids.

By way of example, a strain of Bt kurstaki at the same time expressing the cryIAc gene under the control of its own promoter and the cryIC gene under the control of the promoter of the cryIIIA gene.

Among the cry genes utilizable in these constructs, it is possible to cite: cryI, cry II, cry IV and cyt.

Another method of introduction of a gene to be expressed consists in using Gram-positive bacterial plasmids having a functional replication origin in Bt which is described, for example, in the patent application PCT W093/02199 concerning the pHT304 and pHT315 plasmids.

The sigK⁻ strains obtained according to the process according to the invention are utilizable, optionally after inactivation, in pesticidal compositions, in particular in insecticidal compositions intended to be used in order to destroy larvae, in particular insect larvae. The pesticidal compositions will be prepared according to techniques known per se, that is to say, if this is necessary, as a mixture with an inert or noninert support ensuring an optimum activity of the Bacillus toxins concerned.

The inactivation of the strains, which is essential for the utilization of the sporulating strains in certain countries, is optional in the case of the sigK⁻ mutants constructed in the context of the present invention. This inactivation can be carried out by any physical or chemical method, especially by irradiation, which ensures the non-viability of the strains. The strains according to the invention do not have any viable spores, their inactivation is easier than in the sporulated strains case.

As has been indicated above, the toxins being kept in the interior of the bacteria allows the length of life of the toxins in the environment (the toxin only being liberated during the digestion of the bacterium by the larva) to be increased. However, it has been possible to demonstrate the fact that certain mutants according to the invention have a resistance which is quite exceptional, in this case it is necessary to provide for either the use of selected specific strains for their good digestibility in the insects to be treated, or alternatively to provide for chemical treatments, surface-active agents for example, physical treatments, treatments with ultrasound, or biological treatments, introduction of particular elements into the walls of the microorganism (by genetic recombination technique or others) in order to ensure a better digestibility or an easier accessibility of the toxin when the microorganism has been ingested.

This novel strain of Bt is capable of supplying one of the elements to a pesticidal composition, but is likewise useful as a vector for expressing homologous or heterologous genes with respect to the genome of Bt, the said genes being cloned in the sigK⁻ mutant of Bt, either with the aid of a self-replicating plasmid, or by homologous recombination with respect to the genome of the bacterium.

The construction of the vector system which can express, for example, proteases, lipases or any other type of protein, may be similar to that described in the patent application PCT W094/25612.

The invention likewise relates to a nucleotide sequence containing the SigE gene, not containing any active SigK gene and containing a sequence coding for a gene of interest.

BRIEF DESCRIPTION OF THE FIGURES

Other characteristics and advantages of the present invention will appear on reading the examples below and in referring to the figures in which:

FIG. 1 represents the interruption of the sigE and sigK chromosomal genes of Bacillus thuringiensis; the pAB1 and pAB2 plasmids are integrated into the Bt chromosome by homologous recombination, the second event of homologous recombination leads to the loss of all the pRN5101 sequence; the arrows indicate the transcription direction of the $Ap^R$, $Em^R$ and $Km^R$ genes which correspond to the genes conferring, respectively, resistance to ampicillin, erythromycin and kanamycin, the triangles represent, respectively, the replication origin of pBR322 (oriEc) and the replication origin of pE194ts (orits);

Figure 3A:
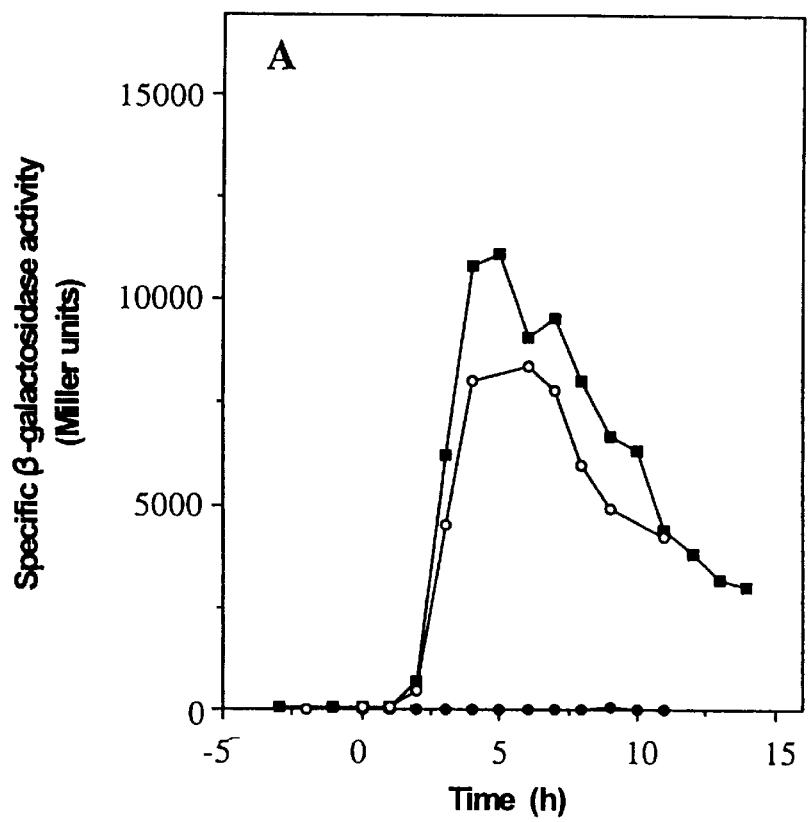
Figure 3B:
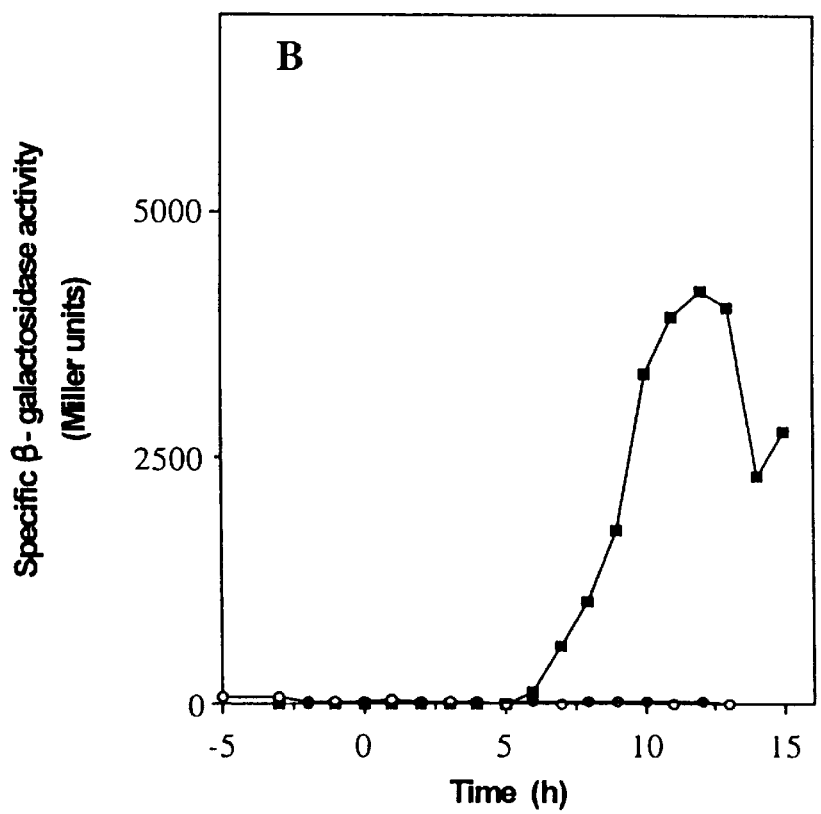
Figure 4:
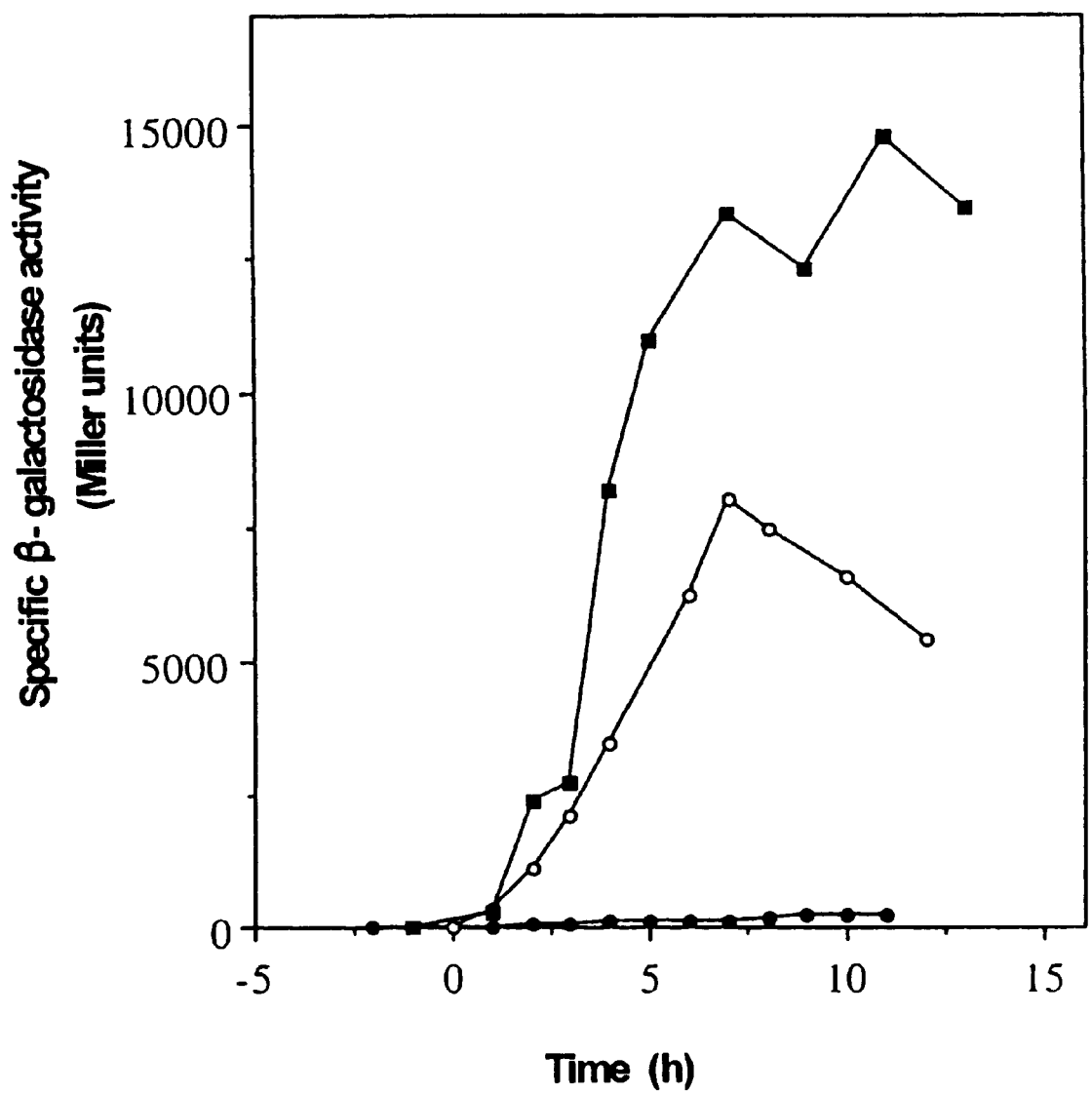
Figure 6A:
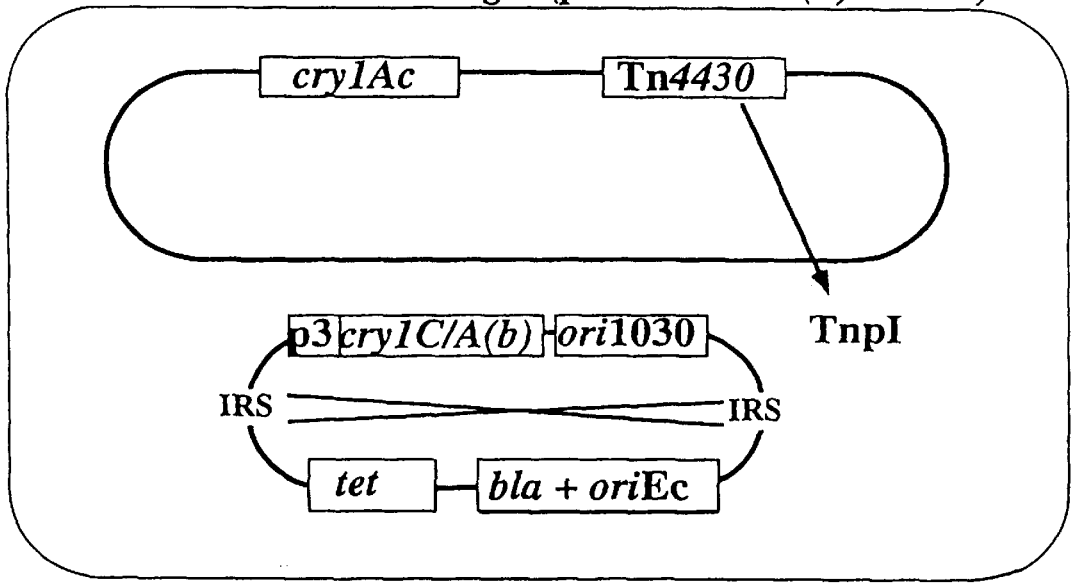
Figure 6B:
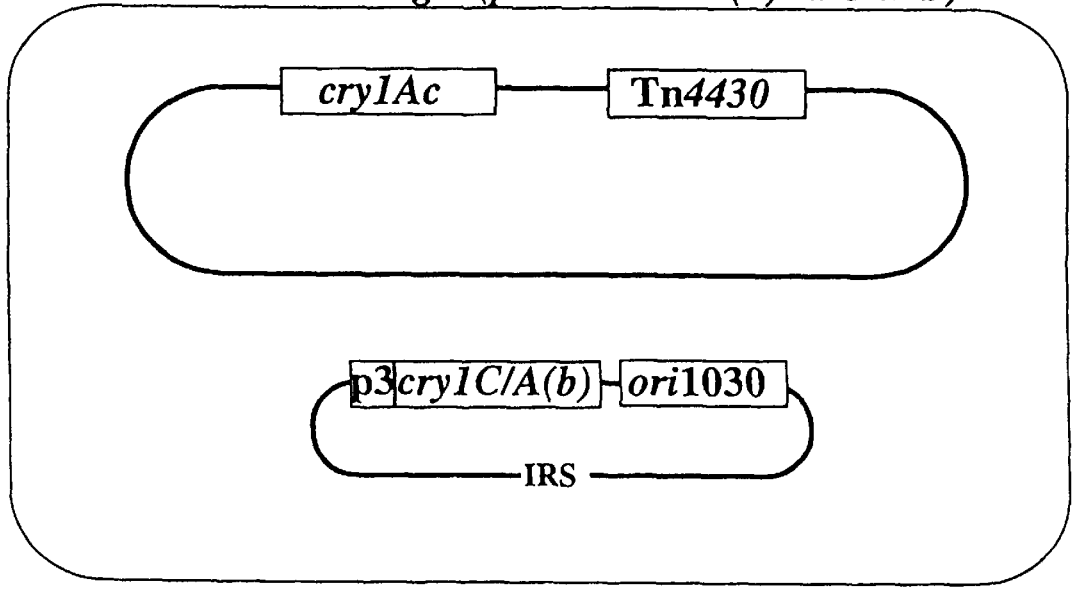

the arrows indicate the transcription direction of ermC, bla and lacZ and the functional replication direction in E. coli (oriEc); ori1030 is the replication origin of the Bt pHT1030 plasmid (Lereclus and Arantes 1992); the broken arrows indicate the transcription direction initiated starting from the promoter psigE, psigK, Bt I and Bt II, as has been indicated above (Rong et al. 1986; Sandman et al. 1988; Wong et al. 1983); the HindIII-BamHI fragments carrying the promoter regions of the spoIID, cotA and cryIAa genes have been cloned in pHT304-18Z;

FIG. 3 represents the expression of β-galactosidase in Bt under the control of the promoters of the spoIID and cotA genes; the cells are grown on SP medium at 30° C.; the time zero indicates the end of the exponential phase, tn is the number of hours before or after time zero; FIG. 3A is the β-galactosidase activity of the Bt strain carrying pHTspoIID; FIG. 3B is the β-galactosidase activity of the Bt strain carrying pHTcotA; the specific activity of β-galactosidase is determined at the times indicated in Spo⁺407 (■), 407 SigE⁻ (●) and 407 sigK⁻ (○);

FIG. 4 represents the expression of β-galactosidase directed under the control of cryIAa in the strains of Bt carrying pHTcryIA2, grown on SP medium at 30° C. and the β-galactosidase activity being determined at the times indicated in Spo⁺407 (■), 407 SigE⁻ (●) and 407 SigK⁻ (○);

FIG. 5 represents the pHTF3-1C/A(b) -IRS-T plasmid; this plasmid derives from pBluescript II KS⁻ (the DNA of pBluescript II KS⁻ being represented by the "bla+oriec" box), it carries two sequences containing the internal resolution site (IRS of the Tn4430 transposon (Lereclus et al., 1986) located directly on both sides of the pBluescript II KS⁻ and of a tet gene conferring resistance to tetracycline coming from Bacillus cereus, it contains, in addition, the coding part of the cryIC/A (b) chimeric gene under the control of the p3 promoter of cryIIIA (Agaisse and Lereclus, 1994) and the replication origin of the pHT1030 plasmid of B. thuringiensis (Lereclus and Arantes, 1992);

FIGS. 6A and 6B represent the recombination reaction between the two IRS sites, catalyzed by the TnpI integrase of the Tn4430 transposon present in the Kto SigK⁻ strain, the plasmid originating from the site-specific recombination is designated pHTF3-IC/A(b)-IRS-T-Δ.

EXAMPLE 1

Material and methods

Bacterial strains and media

The strain Bt 407 (H1 serotype) and its acrystal-liferous derivative (Cry⁻) have been isolated by O. Arantes as has been described above (Lereclus et al. 1989). $E.$ $coli$ K-12 strain TG1 (Δ(lac-proAB) supE thi hsd D5 (F'traD36 pro⁺ proB⁺laclq lacZ ΔM15)) is used for the cloning experiments (Gibson 1984). The Bt strains are cultured at 30° C. in a Luria medium (LB) and in HCT medium (Lecadet et al. 1980) or in a sporulation nutrient medium (SP medium) (Lereclus et al. 1995). The $E.$ $coli$ strains are cultured at 37° C. in an LB medium. The antibiotic concentration for the bacterial selection is as follows: ampicillin, 100 μg/ml (for $E.$ $coli$); erythromycin, −5 μg/ml (for Bt); kanamycin, 10 μg/ml for $E.$ $coli$ and 200 μg/ml for Bt.

Plasmids and DNA fragments

The pRN5101 plasmid which was supplied by S. Gruss is a heat-sensitive replication origin plasmid in Gram-positive organisms, it was constructed by insertion of pE194ts (Villafane et al. 1987) into the ClaI site of pBR322. The Bluescript plasmid (pBS KS⁻) comes from Stratagene and the pHT304-18Z and pHT410 plasmid constructs have already been described (Agaisse and Lereclus 1994b; Lereclus et al. 1989). The oligonucleotides (Cry1A-1 and Cry1A-2) used for the PCR amplification of the 362 bp fragment containing the promoter region of the Cry1Aa gene (Wong et al. 1983) are described in Table 1. The Cry1A-1 primer has a 7 bp extension at the 5' end containing the HindIII restriction site and the Cry1A-2 primer contains an 8 bp extension with the BamHI restriction site. The two restriction sites are introduced to facilitate cloning in pHT304-18Z. To interrupt the Bt sigE and sigK genes, the 5' and 3' regions of the corresponding genes are amplified by PCR using oligonucleotides with appropriate restriction sites at the 5' end (Table 1) and sub-cloned separately in pBS KS⁻. The 5' regions of the sigE and sigK genes are 857 and 611 bp restriction fragments of BamHI-XbaI respectively. The 3' regions are 807 and 606 bp EcoRI-BamHI restriction fragments respectively. The DNA fragments containing the 5' and 3' regions of each of the genes are purified and bound to a 1.5 kb XbaI-EcoRI fragment carrying the aphA3 gene of Enterococcus faecalis ($Km^R$ cassette) (Trieu-Cuot and Courvalin 1983) in the BamHI restriction site of the pRN5101 plasmid. The resultant heat-sensitive plasmids pAB1 and pAB2 carry a copy interrupted by a kanamycin resistance gene in the sigE and sigK genes respectively.

The plasmids pDG675 and pDG676 respectively carrying the promoter region of the spoIID and cotA genes of $B.$ $subtilis$ were supplied by Dr. P. Stragier (Institut de Biologie Physico-Chimique, Paris, France). pHTspoIID was constructed by sub-cloning the 300 bp HindIII-BamHI restriction fragment of pDG675 between the HindIII and BamHI restriction sites of pHT304-18Z. pHTcotA was constructed as follows: the 400 bp of the EcoRI-BamHI fragment of pDG676 are initially sub-cloned in pBS KS⁻, giving pKScotA. The HindIII-BamHI restriction fragment of pKScotA is then sub-cloned between the HindIII and BamHI restriction sites of pHT304-18Z, the resultant plasmid being designated by the name pHTcotA.

Construction and transformation

The plasmid DNA is extracted from $E.$ $coli$ by the standard alkaline lysis process. The chromosomal DNA is extracted from Bt as has been described previously (Msadek et al. 1990). The restriction enzymes and the T4 ligase come from New England Biolabs, Beverly, Mass. The DNA fragments are purified on agarose gel using the Prep-A-Gene kit (BioRad Laboratories, Richmond, Calif.). The oligonucleotide primers are synthesized by Genset (Paris, France) and the PCR amplification is carried out using the GeneAmp PCR 2400 system (Perkin-Elmer, Foster City, Calif.). The DNA matrix used in the PCR amplficiation is either the cryIAa gene already cloned from the Bt 407 strain (Lereclus et al. 1989) or the chromosomal DNA extracted from the 407 Cry⁻ strain. The reaction conditions are as follows: a 5 min. incubation at 95° C., followed by 30 one min. cycles at 57° C. for the hybridization, one min. at 72° C. for the extension and one min. at 92° C. for the denaturation; finally, a new incubation at 72° C. for 10 min. is carried out. The Taq polymerase comes from USB Laboratories (Cleveland, Ohio). The standard procedure is used for the transformation of $E.$ $coli$ and the Bt strains are transformed by electroporation, as has already been described (Lereclus et al. 1989).

The protein analysis is carried out after culture of the Bt strains and sonication, the analysis being carried out on 0.1% SDS–12% PAGE.

Bioassays of insecticidal activity

The toxicity of the preparations is estimated using the larva of $Plutella$ $xylostella$ in the second stage and the free ingestion technique as has been described previously (Sanchis et al. 1988).

EXAMPLE 2

Construction of the SigE⁻ and sigK⁻ mutants of Bt

The pAB1 and pAB2 heat-sensitive plasmids containing the copy of the gene interrupted by $Km^R$ of sigE and sigK respectively are introduced into the Bt 407 Cry⁻ strain by electroporation. The replacement of the sigE and sigK genes by the sigE::Km and sigK::Km interrupted copy is obtained by successive cultures of transformants in the presence of kanamycin at a non-permissive temperature (40° C.) (see FIG. 1). As emerges from FIG. 1, the Bt strains transformed by the pAB1 or pAB2 plasmids are all resistant both to erythromycin and to kanamycin at 37° C.

The transformants in which the sigE or sigK gene has been exchanged for its interrupted copy are cultured at a non-permissive temperature, that is to say at which the replication of the plasmids has been blocked. They can be selected by their resistance to kanamycin. The Spo⁻ mutants (407-SigE⁻ and 407-SigK⁻ below) are resistant to kanamycin but sensitive to erythromycin. The replacement of the Bt sigE and sigK genes by their interrupted copy is checked by PCR analysis, the chromosomal DNA of the selected mutants is used as a matrix for the PCR and the complementary external sequences of each gene are used as a primer in combination with sigE-4 and sigK-4 oligonucleotides respectively. The size of the PCR products corresponds to genes interrupted by $Km^R$.

The Bt SigE⁻ and SigK⁻ mutant strains are incapable of sporulating. No heat-resistant spore is produced after 72 hours of growth at 30° C. in HCT or SP medium. Using similar growth conditions, at least 90% of the cells of the wild strain sporulate after 24 or 48 hours. The examination of the cells by phase-contrast microscopy indicates that the sigE⁻ mutant strain is blocked at an early sporulation stage (stage II), after the formation of the asymmetric septum dividing the mother cell and the spore compartment. The sigK⁻ mutant strain is blocked in a later sporulation stage (stage IV). A gray prespore situated at one of the poles of the cell can be observed in the interior of the cells.

Figure 2:
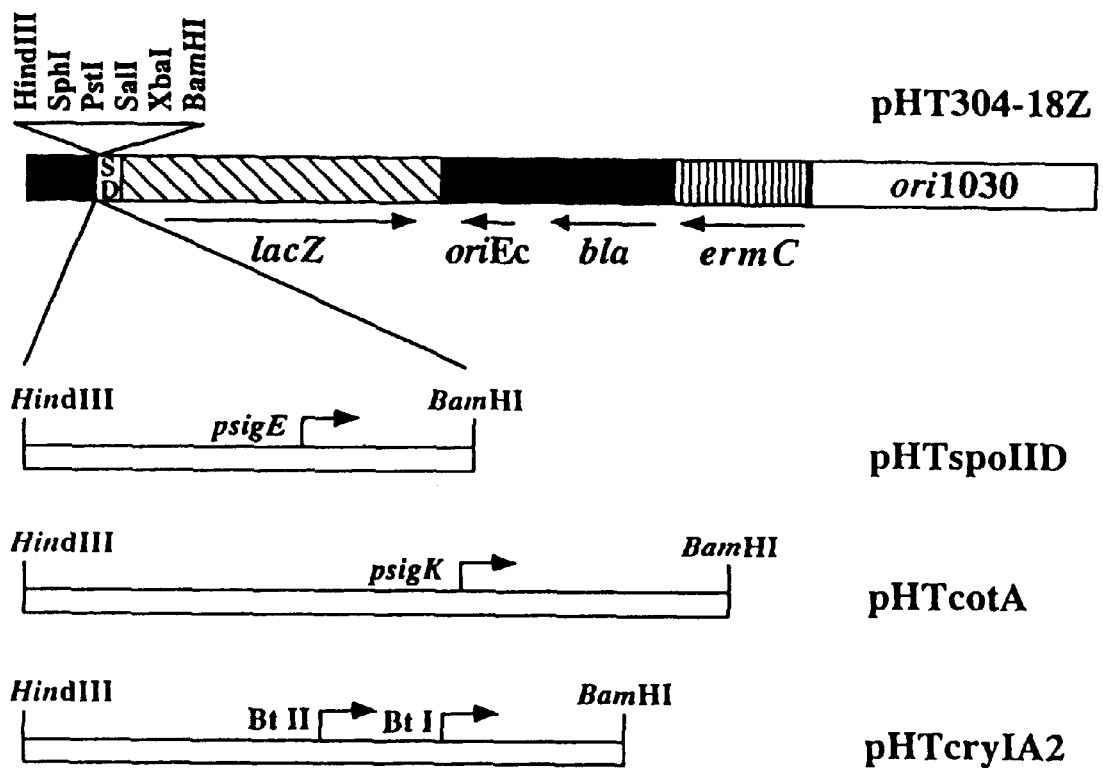
FIG. 2 represents the construction of the plasmids for the analysis of transcription in Bacillus thuringiensis; pHT304-18Z is [sic], as has been previously described (Agaisse and Lereclus 1994b)

The pHTspoIID and pHTcotA plasmids (see FIG. 2) carrying the promoter regions of the spoIID and cotA genes of Bacillus subtilis fused with the lacZ gene are constructed to follow the appearance and the disappearance of the σE and σK factors during the sporulation of Bt. spoIID is transcribed by an RNA polymerase containing the σE factor (Lopez-Diaz et al. 1986; Rong et al. 1986). This gene is involved in the morphological development of the spores at stage II (Young and Mandelstam 1979). The cotA gene codes for a spore envelope protein (Donavan et al. 1987) and its transcription depends on σK (Sandman et al. 1988). The pHTspoIID and pHTcotA plasmids are introduced into Bt 407 Cry⁻ Spo⁺, 407-SigE⁻ and 407-SigK⁻ by electroporation and the synthesis of β-galactosidase is followed during growth in SP medium (FIGS. 3A and 3B). In the Spo⁺ strain, the synthesis of β-galactosidase under the control of the spoIID promoter starts at t2 to attain a maximum of approximately 10,000 U/mg of proteins at t5 and then decreases. In the strain in which the synthesis of β-galactosidase is under the control of the cotA promoter, this is detected only at t6 and attains a maximum of 4000 U/mg of proteins at t11. There is no detectable expression of β-galactosidase (less than 10 U/mg of proteins) in the 407-SigE⁻ mutant for the spoIID' or cotA'-'lacZ transcriptional fusions. As the transcription of sigK depends on σE (Sandman et al. 1988) there is no production of the factor K in this mutant strain. There is no detectable expression of lacZ starting from the cotA promoter in the 407-SigK⁻ mutant and the expression starting from the spoIID promoter has a maximum at t6 as in the wild strain.

EXAMPLE 3
Expression of cry1Aa'-'lacZ in SigE⁻ and SigK⁻ mutants of Bt

To determine the temporal regulation of the promoters of the cry1Aa gene in the wild strain of Bt and in the Spo⁻ mutants, a plasmid containing the cry1Aa'-lacZ [sic] transcriptional fusion was constructed. A region containing the promoter region of the cry1Aa gene is amplified by PCR, as has been described, then cloned in pHT304-18Z upstream of the lacZ reporter gene. The resultant plasmid, designated by the name pHTcry1A2 (FIG. 2), is introduced into the Bt 407 Cry⁻ Spo⁺, 407 SigE⁻ and 407 SigK⁻ strains by electroporation. The production of β-galactosidase in the Spo⁺ 407 Cry⁻ strain starts at t2 and has two peaks, the first at t7 and the second at t11 (FIG. 4). As has been indicated for the spoIID'-'lacZ and cotA'-'lacZ fusions, t7 and t11 correspond to the maximal periods of expression of σE and σK. The expression of the synthesis of β-galactosidase directed by the promoter region of cry1Aa is severely reduced in the 407-SigE⁻ mutants (FIG. 4). However, a slight β-galactosidase activity is detected at t2 with a maximum of 200 U/mg of proteins at t10. The β-galactosidase synthesis directed by the promoter region of cry1Aa starts at t2 and shows a maximum of 9000 U/mg of proteins at t7 in the mutant 407-SigK⁻ (FIG. 4). The second expression peak at a later sporulation time in the Spo⁺strain is not apparent in the SigK⁻ mutant, which indicates a participation of the σK factor in the transcription of the cry1Aa gene during the late sporulation phase.

EXAMPLE 4
Production of the Cry1Aa toxin in the SigE and SigK mutants of Bt

The pHT410 plasmid carrying the cry1Aa gene of the wild strain of Bt 407 (Lereclus et al. 1989) is introduced into the Bt 407 Cry⁻ Spo⁺ 407-SigE⁻ and 407-SigK⁻ strains by electroporation.

The transformants are cultured on HCT and SP medium at 30° C. and the production of crystalline inclusions is examined by phase-contrast microscopy and .electron microscopy. After 48 hours' growth in the HCT medium, the wide bipyramidal crystals are observed in the 407-Spo⁺ and 407-SigK⁻ transformants. However, the crystals in the Spo⁺ strain are liberated while those of the SigK⁻ mutants remain encapsulated in the cell wall. Even after 72 hours' growth in the HCT medium, there is no liberation of the crystalline inclusions from the SigK⁻ mutant. No crystal is observed in the 407-SigE⁻ strain carrying the pHT410 plasmid.

An SDS-PAGE analysis of the proteins contained in the crystal-cell and spore-crystal preparations from cells grown on HCT medium show that the 407-SigE⁻ strain carrying pHT410 does not produce the Cry1Aa polypeptide of 130 kDa, unlike the 407-SigK⁻ strain carrying pHT410 which produces a toxin similar to that obtained from the 407 Cry⁻ Spo⁺ strain containing the same plasmid.

The insecticidal activity of the spore-crystal and cell-crystal preparations is analyzed using larvae of *Plutella xylostella* Lepidoptera at the second stage (Table 2). Having taken account of the presence of proteins other than Cry1Aa in the 407-SigK⁻ mutant, it is not possible to determine the precise concentration of toxin in the crystalline preparation of this strain. This is why the LD50 is defined in terms of culture volume to estimate the insecticidal activity of these products. The bioassays indicate that the Cry1Aa toxin produced in 407-SigK⁻ is very toxic for the larvae of *P. xylostella*. However, the insecticidal activity of these products is significantly increased by sonication.

The *Bacillus thuringiensis* strain, which does not express, or only very weakly expresses, the sigma K protein under the experimental conditions above and which is deposited at the CNCM under the No. I-1634 is constructed under the following conditions:

Bacterial strain including the sigK gene is interrupted by the aphA3 gene conferring resistance to kanamycin. The strain thus constructed in transformed by the pHT410 plasmid carrying the Cry1Aa gene and the ermC gene, conferring resistance to erythromycin. This nonsporulating strain produces significant quantities of Cry1Aa toxin during stationary phase 1a.

EXAMPLE 5
Construction of a recombinant strain of *B. thuringiensis* designated Kto SigK⁻ (PHTF3-IC/A(b)-IRS-T-Δ) expressing a gene coding for a Cry1C/Cry1A(b) chimeric δ-endotoxin under the control of the promoter of the cryIIIA gene The Kto strain is a natural sporulating strain of *B. thuringiensis;* this strain synthesizes a δ-endotoxin of Cry1A(c) type. This δ-endotoxin has an insecticidal activity against the larvae of *Ostrinia nubilalis* (European corn borer), a major pest of maize crops in the United States and in Europe. This δ-endotoxin (and thus the strain Kto) is, on the other hand, not very active against other important pests belonging to the Noctuidae family such as *Spodoptera littoralis, Spodoptera exigua* or *Mamestra brassicae* (see Table 3). Conversely, the Cry1C δ-endotoxin or the Cry1C/Cry1A(b) chimeric δ-endotoxin, designated Cry1C/A(b) below, whose construction (PHT81 plasmid) is additionally described by Sanchis et al. (1989), are active against *S. littoralis* but not very active against *O. nubilalis* (Table 3).

In order to increase the spectrum of activity of the Kto strain, it was of interest to introduce the cry1C gene or the chimeric cry1C/A (b) gene into the Kto strain. However, it has been shown that the introduction of a cry1-type gene (dependent on sporulation) into a strain of *B. thuringiensis* already containing one or more other δ-endotoxin genes, whose expression likewise depends on sigma E and sigma K sporulation factors, is not interpreted by an increase in the total production of δ-endotoxins. Consequently, a recombinant strain containing different genes of cry1 type will have a wider spectrum of activity but will produce less of each of the δ-endotoxins; it will thus have a lower effectiveness with respect to each of the target insects than strains producing a sole δ-endotoxin specific for each of the targeted insects. This phenomenon can be explained by a titration effect of the sigma factors of sporulation by the promoters of different cry1 genes present in the strain. In order to resolve this problem, it has recently been shown (Sanchis et al., 1996) that it is possible to place the gene coding for the Cry1C protein under the control of the promoter of the cryIIIA gene, whose expression is independent of the sigma sporulation factors (Agaisse and Lereclus, 1994).

The cry1C gene, under the control of the cryIIIA promoter, was introduced into the Kto strain to give the recombinant Kto(pHTF3-1C-IRS-Δ) strain (Sanchis et al., 1996). This recombinant strain at the same time produces the Cry1A(c) and Cry1C toxins and the quantity of δ-endotoxins produced is increased by a factor of 1.5 to 2 with respect to the parent strain. The increase in the total production of the two δ-endotoxins Cry1A(c) and Cry1C obtained in the strain Kto(pHTF3-1C-IRS-A) probably results from the fact that the expression of the cry1C gene in this strain does not depend on specific sigma factors of sporulation; it thus does not interfere with that of the cry1A(c) gene which is dependent on sporulation. In order to construct the Kto SigK⁻ (pHTF3-1C/A(b)-IRS-T-Δ) strain described here, the gene coding for the chimeric Δ-endotoxin Cry1C/A(b) whose activity with respect to *S. littoralis* is slightly superior to that of Cry1C has been placed under the control of the promoter of the cryIIIA gene, as described previously for the cry1c gene (Sanchis et al., 1996).

Figure 1:
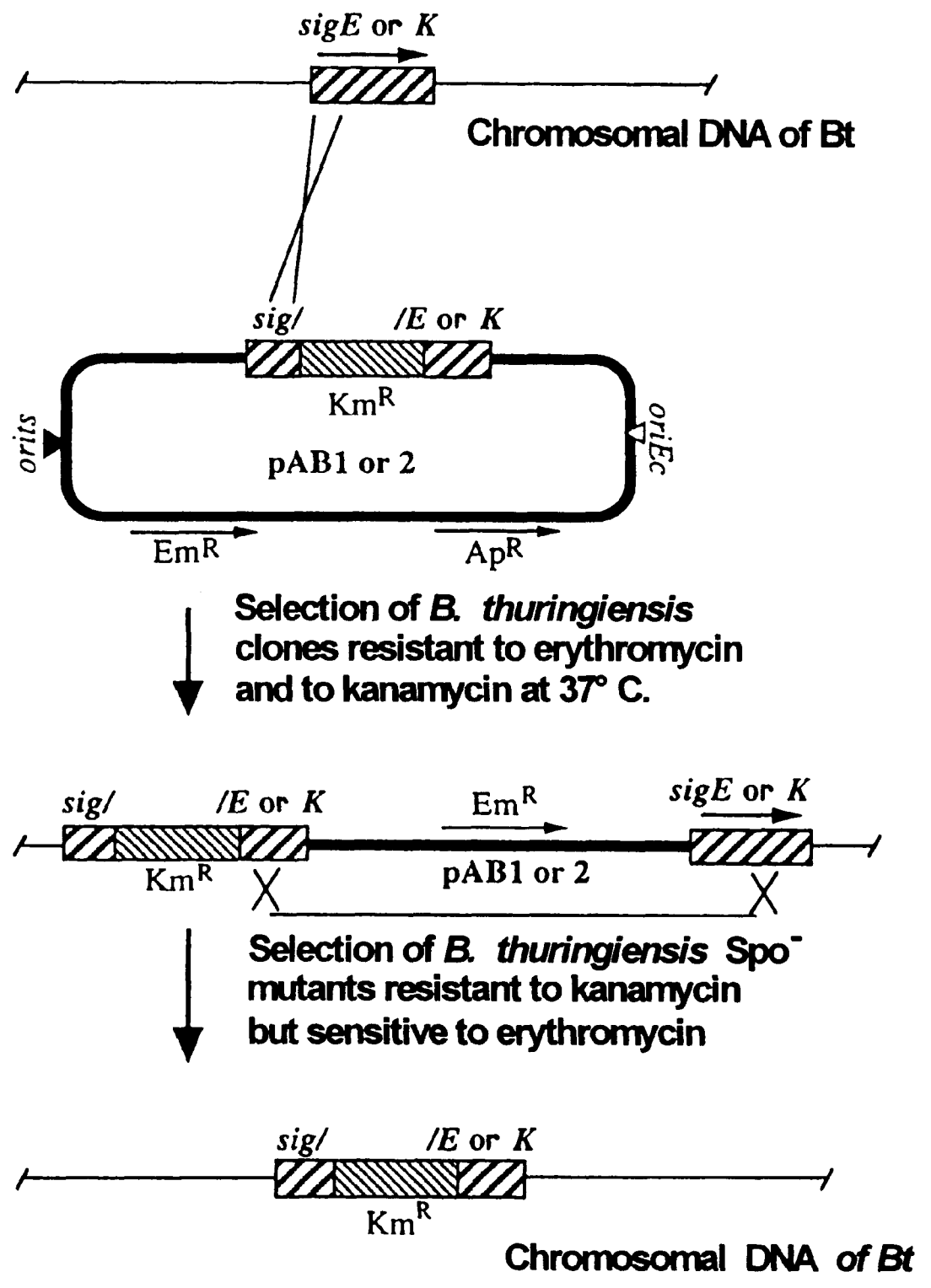

Likewise, a sigK⁻ mutant (whose sigK gene is interrupted by the aphA3 gene) of the Kto strain was constructed as described in Example 2 with the aid of the pAB2 plasmid (see FIG. 1). When the Kto SigK⁻ strain, which is an Spo⁻ mutant of Bt, is cultured at 30° C. in HCT medium for 48 hours, it produces significant quantities of the Cry1A(c) δ-endotoxin which accumulates in the form of a crystalline inclusion which remains encapsulated in the cell, which does not lyze. The activity of the Kto SigK⁻ strain with respect to *O. nubilalis* is equivalent to that of the Kto parent strain, whether the Kto SigK⁻ strain has previously been sonicated or not.

The Kto SigK⁻ strain was then transformed with the pHTF3-1C/A(b)-IRS-T plasmid (see FIG. 5). This plasmid, derived from pBluescript II KS⁻, carries two sequences containing the internal resolution site (IRS) of the Tn4430 transposon (Lereclus et al., 1986). These two IRSs are located directly on both sides of the pBluescript II KS⁻ and of a tet gene conferring resistance to tetracycline and coming from *Bacillus cereus*. In addition, the pHTF3-1C/A(b)-IRS-T contains the coding part of the chimeric cry1C/A(b) gene under the control of the p3 promoter of cryIIIA and the replication origin of the pHT1030 plasmid of *B. thuringiensis* (Lereclus and Arantes, 1992).

After transformation, the TnpI integrase of the Tn4430 transposon present in the Kto SigK⁻ strain catalyzes a recombination reaction between the two IRS sites and the DNA contained between these two sites is excised. Of the two cyclic molecules resulting from the recombination, only that which carries the replication origin of the pHT1030 plasmid and the chimeric cry1C/A(b) gene can be replicated and the plasmid thus obtained, designated pHTF3-1C/A(b)-IRS-T-Δ, has lost the DNA corresponding to the pBluescript II KS⁻ and to the tet gene (see FIG. 6). The Kto SigK⁻ (pHTF3-1C/A(b)-IRS-T-Δ) recombinant strain produces both the Cry1A(c) and the Cry1C/A(b) δ-endotoxins in significant quantity and thus has the advantage of having a wider spectrum of activity than the parent Kto or Kto SigK⁻ strain (Table 4).

In addition, such a strain has two other advantages:

1.) The Cry1A(c) and Cry1C/A(b) δ-endotoxins remain encapsulated in the cell. This could be interpreted by an increase in the persistence of the toxins in the treated crop zone, because of the physical protection which this could confer on them against degradation and UV radiation after spreading.

2.) The sigK⁻ mutant is an Spo⁻ mutant blocked at stage IV of the sporulation process and thus does not produce a viable spore; the use of such a mutant allows the dissemination of spores into the environment during insecticidal treatment to be avoided.

TABLE 1

| Primer | Sequence | Position bpᵃ | Restriction site at the 5'end | |
|---|---|---|---|---|
| cryIA-1 | 5'CCCAAGCTTGCAGGTAAATGGTTCTAAC3' | 156–177* | HindIII | (SEQ ID NO:1) |
| cryIA-2 | 5'CGCGGATCCATCTCTTTTATTAAGATACC3' | 495–518* | BamHI | (SEQ ID NO:2) |
| sigE-1 | 5'CGGGATCCCGTTGAAAGCGTAGAGGTCAGAA3' | 16–38** | BamHI | (SEQ ID NO:3) |
| sigE-2 | 5'GCTCTAGAGCCAACGCGATGCATATGTTGCTA3' | 834–855** | XbaI | (SEQ ID NO:4) |
| sigE-3 | 5'GGAATTCCATTGTCTGACGTGTTAGGTACA3' | 961–982** | EcoRI | (SEQ ID NO:5) |
| sigE-4 | 5'CGGGATCCCGATACGCAATATCTCGCAATGA3' | 1730–1751** | BamHI | (SEQ ID NO:6) |
| sigK-1 | 5'CGGGATCCCGTCCAGTTATAATTTGAGCTCCAA3' | 31–53** | BamHI | (SEQ ID NO:7) |
| sigK-2 | 5'GCTCTAGAGCCCCGATTGTACCAATTGAAAT3' | 603–623** | XbaI | (SEQ ID NO:8) |
| sigK-3 | 5'GGAATTCCATTAAAGCGATCGAGAGCTATT3' | 627–648** | EcoRI | (SEQ ID NO:9) |
| sigK-4 | 5'CGGGATCCCGGCACCTTCTAATATTACAGATAGA A3' | 1194–1217** | BamHI | (SEQ ID NO:10) |

TABLE 1-continued

| Primer | Sequence | Position bp[a] | Restriction site at the 5' end | |
|---|---|---|---|---|
| sigE-Ch | 5'TTTTCTAAAAAGCGTATTGAA3' | 1-22** | any | (SEQ ID NO:11) |
| sigK-Ch | 5'GGAGAAACCATAGTTATGAA3' | 1-20** | any | (SEQ ID NO:12) |

[a]The position of the oligonucleotides is determined from:
*Wong et al. 1983 and
**Adams et al. 1991

TABLE 2

Insecticidal activity of Bt strains

| Strain | LD50[a] µl/ml of powdered food[b] |
|---|---|
| 407 Spo⁺ (pHT410) | 14.7 (7.9–21.8) |
| 407-SigK⁻ (pHT410) | 124.6 (68.6–1358.7) |
| 407-SigK⁻ (pHT410) sonicated for 1 min.[c] | 35.6 (15.2–71.2) |
| 407-SigK⁻ (pHT410) sonicated for 5 min.[d] | 9.5 (6.2–12.6) |

[a]The LD50 is the volume of preparation necessary to kill 50% of the insect larvae
[b]µl of spore-crystal or cell-crystal solution used per ml of solution spread on the leaves
[c]The cells are partially disrupted by sonication for 1 min., the majority of the crystalline inclusions remain in the interior of the cells
[d]The cells are totally disrupted by sonication for 5 min., 95% of the crystals are liberated

TABLE 3

Activity of Cry1A(c), Cry1C and Cry1C/A(b) δ-endotoxins compared with respect to S. littoralis and O. nubilalis

| δ-Endotoxins | LC50[(1)] with respect to larvae of the second stage in ng of protein/cm² | |
|---|---|---|
| | S. littoralis | O. nubilalis |
| Cry1A(c) | 1000 | 2 |
| Cry1C | 70 | >250 |
| Cry1C/A(b) | 20 | 87 |

[(1)]The LC50, or lethal concentration 50, is the concentration of δ-endotoxins which is necessary to kill 50% of the treated population after 5 days; the biological tests were carried out as described by Sanchis et al. 1996

TABLE 4

Insecticidal activity of strains of Bacillus thuringiensis

| Strain | Characteristics of the strain | LC50[(1)] with respect to larvae of the second stage in ng of protein/cm² | |
|---|---|---|---|
| | | S. littoralis | O. nubilalis |
| Kto | Natural Spo⁺ strain producing Cry1A(c) | 981 (758–1270) | 1.7 (0.9–3) |
| Kto (pHTF3-1C-IRS-Δ) | Kto Spo⁺ strain producing Cry1A(c) and Cry1C | 25 (13–50) | <4.2 |
| Kto SigK⁻ | Kto⁻ Spo⁻ strain | 11 | 2.6 |

TABLE 4-continued

Insecticidal activity of strains of Bacillus thuringiensis

| Strain | Characteristics of the strain | LC50[(1)] with respect to larvae of the second stage in ng of protein/cm² | |
|---|---|---|---|
| | | S. littoralis | O. nubilalis |
| (pHTF3-1C/A(b)-IRS-T-Δ) | producing Cry1A(c) and Cry1C/A(b) in encapsulated form | (3–36) | (0.06–110) |

[(1)]The LC50 is the concentration which is necessary to kill 50% of the treated population in 5 days; the values in brackets represent the 95% confidence intervals; the biological tests were carried out as described by Sanchis et al. (1996).

REFERENCES

Adams L. F., Brown K. L., Whiteley H. R. (1991) Molecular Cloning and characterization of two genes encoding sigma factors that direct transcription from a Bacillus thuringiensis crystal protein gene promoter. J. Bacteriol. 183: 3846–3854.

Agaisse H. and Lereclus D. (1994). Expression in Bacillus subtilis of the Bacillus thuringiensis cryIIIA toxin gene is not dependent on a sporulation-specific sigma factor and is increased in a spo0A mutant. J. Bacteriol., 176: 4734–4741.

Agaisse H. and Lereclus D. (1994b) Structural and functional analysis of the promoter region involved in full expression of the cryIIIA toxin gene of Bacillus thuringiensis. Mol. Microbiol. 13: 97–107.

Donavan W. P., Zheng L., Sandman K., Lobsick R. (1987) Genes encoding spore coat polypeptides from Bacillus subtilis. J. Mol. Biol. 196: 1–10.

Dulmage H. T. (1970) Insecticidal activity of HD-1, a new isolate of Bacillus thuringiensis var. alesti J. Invert. Pathol. 15, 232–239.

Gibson T. J. (1984) Studies on the Epstein-Barr virus genome.

Lecadet M. M., Blondel M. O., Ribier J. (1980) Generalized transduction in Bacillus thuringiensis var. berliner 1715, using bacteriophage CP54 Ber. J. Gen. Microbiol. 121: 203–212.

Lereclus D., Mahillon J., Menou G. and Lecadet M-M. (1986). Identification of Tn4430 a transposon of Bacillus thuringiensis functional in Escherichia coli. Mol. Gen. Genet., 204: 52–57.

Lereclus D. and Arantes O. (1992). spbA locus ensures the segregational stability of pHT1030, a novel type of Gram-positive replicon. Mol. Microbiol., 7: 35–46.

Lereclus D., Agaisse H., Gominet M., Chaufaux J. (1995) Overproduction of encapsulated insecticidal crystal proteins in a *Bacillus thuringiensis* spo0A mutant. Bio/Technology 13: 67–71.

Lereclus D., Arantes O., Chaufaux J., Lecadet M. M. (1989) Transformation and expression of a cloned δ-endotoxin gene in *Bacillus thuringiensis*—FEMS Microbiol. Lett. 60: 211–218.

Lopez-Diaz I., Clarke S., Mandelstam J. (1986) SpoIID operon of Bacillus subtilis: cloning and sequence. J. Gen. Microbiol. 132: 341–354.

Msadek T., Kunst F., Henner D., Klier A., Rapoport G., Dedonder R. (1990) Signal transduction pathway controlling synthesis of a class of degradative enzymes in *Bacillus subtilis:* expression of the regulatory genes and analysis of mutations in degS and degu. J. Bacteriol. 172: 824–834.

Rong S., Rozenkrantz M. S., Sonenshein A. L. (1986) Transcriptional control of the *Bacillus subtilis* spoIID gene. J. Bacteriol. 165: 771–779.

Sanchis V., Lereclus D., Menous G., Chaufaux J., Lecadet M. M. (1988) Multiplicity of δ-endotoxin genes with different specificities in *Bacillus thuringiensis aizawai* 7.29. Mol. Microbiol. 2: 393–404.

Sanchis V., Lereclus D., Menou G., Chaufaux J., Guo S. and Lecadet M. M. (1989). Nucleotide sequence and analysis of the N-terminal coding region of the Spodoptera active β-endotoxin gene of *Bacillus thuringiensis aizawai* 7–29. Mol. Microbiol., 3: 229–238.

Sanchis V., Agaisse H., Chaufaux J. and Lereclus D. (1996). Construction of new insecticidal *Bacillus thuringiensis* recombinant strains by using the sporulation non-dependent expression system of cryIIIa and a site specific recombinaison [sic] vector. J. Biotechnol., 48: 81–96.

Sandman K. L., Kroos L., Cutting S., Youngman P., Losick R. (1988) Identification of a promoter for a spore coat protein in Bacillus subtilis and studies on the regulation of its induction at a late stage of sporulation. J. Mol. Biol. 200: 461–473.

Trieu-Cuot P., Courvalin P. (1983) Nucleotide sequence of the *Streptococcus faecalis* plasmid gene encoding the 3'5"-aminoglycoside phospho-transferase type III. Gene 23: 331–341.

Villafane R., Bechhofer D. H. Narayanan C. S., Dubnau D. (1987) Replication control genes of plasmid pE194. J. Bacteriol. 169: 4822–4829.

Wong H. C., Schnepf H. E., Whiteley H. R. (1983) Transcriptional and translational star sites for the *Bacillus thuringiensis* crystal protein gene. J. Biol. Chem. 258: 1960–1967.

Young M., Mandelstam J. (1979) Early events during bacterial endospore formation. Adv. Microb. Physiol. 20: 103–162.

Yoshisue H., Nishimoto T., Sakai H., Komano TI (1993) Identification of a promoter for the crystal protein-encoding gene cryIVB from *Bacillus thuringiensis* subsp. *israelensis.* Gene 137: 247–251.

Yoshisue H., Fukada T., Yoshida K.I., Sen K., Kwosawa S. I. Sakai H., Komano T. (1993) Transcriptional Regulation of *Bacillus thuringiensis* subsp. *israelensis.* Mosquito larvicidal crystal protein gene cryIVA. J. Bacterial. 175: 2750–2753.

PCT patent application W094/25612.

PCT patent application W093/02199.

PCT patent application W082/03872.

European patent application 0 178 151.

European patent application 0 224 331,

European patent application 0 192 319.

European patent application 0 228 838.

European patent application 0 295 156.

European patent application 0 349 353.

We claim:

1. A purified culture of *Bacillus Thuringiensis* strain that expresses the SigE gene, and wherein the SigK gene has been interrupted by introduction of a DNA sequence or has been at least partially deleted.

2. The *Bacillus Thuringiensis* strain according to claim 1, wherein the SigK gene has been interrupted by introduction of a DNA sequence conferring a positive selection character on the strain.

3. The *Bacillus Thuringiensis* strain according to claim 2, wherein the positive selection character is resistance to an antibiotic.

4. The *Bacillus Thuringiensis* strain according to claim 1, wherein the Bt strain expresses one or more Cry genes.

5. The *Bacillus Thuringiensis* strain according to claim 4, wherein the Cry gene(s) is/are carried by a vector.

6. The *Bacillus Thuringiensis* strain according to claim 4, wherein the Cry genes are integrated into the chromosome.

7. The *Bacillus Thuringiensis* strain according to claim 1, which expresses a protein of interest carried by a self-replicating plasmid or by a DNA sequence integrated into the chromosome.

8. The *Bacillus Thuringiensis* strain according to claim 7, which contains a DNA sequence in the SigK gene expressing a protein of interest.

9. The *Bacillus Thuringiensis* strain according to claim 7, which contains in replacement of all or part of the SigK gene a DNA sequence expressing a protein of interest.

10. *Bacillus thuringiensis* 407 SigK⁻ (pHT410) deposited at the National Collection of Microorganism Cultures of the Institut Pasteur on Oct. 26, 1995 under the number I-1634.

11. *Bacillus thuringiensis* Kto SigK⁻ (pHTF3-1C/A(b)-IRS-T-Δ) deposited at the National Collection of Microorganism Cultures of the Institut Pasteur on Oct. 22, 1996 under the number I-1776.

12. A Pesticidal composition, comprising an effective amount of a Bt strain wherein the SigK gene has been interrupted by introduction of a DNA sequence or has been at least partially deleted and is toxic to Lepidoptera or Diptera.

13. The composition according to claim 12, wherein the Bt strain has been inactivated.

14. The composition according to claim 13, wherein said Bt strain has been inactivated by physical means.

15. The composition according to claim 13, wherein said Bt strain has been inactivated by irradiation.

16. The composition according to claim 13, wherein, said Bt strain has been inactivated by chemical means.

17. The position according to claim 12, wherein the Bt strain has been treated to improve the digestibility of the strain or alternatively to improve the accessibility of the protein.

18. The composition according to claim 17, wherein the Bt strain has been treated by sonnication.

19. A recombinant polynucleotide containing the SigE gene, wherein the SigK gene has been interrupted by introduction of a DNA sequence or has been at least partially deleted and containing a sequence coding for a gene of interest.

* * * * *